United States Patent [19]

Phillips et al.

[11] 4,263,447

[45] Apr. 21, 1981

[54] PREPARATION OF ALLYLIC CYCLOALKENOLS AND CARBOXYLIC ACID ESTERS THEREOF

[75] Inventors: Benjamin Phillips, Riverside, Conn.; Walter J. Skraba, Sarasota, Fla.; Daniel W. McNeil, New Fairfield, Conn.

[73] Assignee: Union Carbide Corporation, New York, N.Y.

[21] Appl. No.: 58,124

[22] Filed: Jul. 16, 1979

[51] Int. Cl.³ .................. C07C 67/08; C07C 69/03
[52] U.S. Cl. ................................ 560/231; 260/410; 568/821; 568/825; 568/838; 568/700; 560/105; 560/106

[58] Field of Search ............... 568/667, 825, 821, 838, 568/700; 560/241, 105, 106, 231; 260/586 P, 410

[56] References Cited

U.S. PATENT DOCUMENTS

| | | | |
|---|---|---|---|
| 2,223,494 | 12/1940 | Loder | 260/586 P |
| 3,649,675 | 3/1972 | Koehl, Jr. | 560/241 |

*Primary Examiner*—Bernard Helfin
*Attorney, Agent, or Firm*—Bernard Francis Crowe

[57] ABSTRACT

Allylic cycloalkenols and/or allylic cycloalkenol esters are prepared by autoxidation of the corresponding cycloolefins using elemental oxygen contacted with solutions of cycloolefins containing catalytic amounts of soluble cobalt and copper compounds with a carboxylic acid activator.

12 Claims, No Drawings

PREPARATION OF ALLYLIC CYCLOALKENOLS AND CARBOXYLIC ACID ESTERS THEREOF

BACKGROUND OF THE INVENTION

This invention pertains to the preparation of allylic cycloalkenols and more particularly to the autoxidation of the corresponding cycloolefins with elemental oxygen and catalytic amounts of soluble cobalt and copper compounds together with a catalyst activating amount of a carboxylic acid.

Allylic cycloalkenols such as 2-cyclopentenol and 2-cyclohexenol are useful intermediates for the synthesis of polyfunctional epoxides for epoxy resin systems. 2-Cyclopentenol is of particular interest since it can be etherified and then epoxidized to afford bis-(2,3-epoxycyclopentyl) ether, a diepoxide that reacts with aromatic diamines to provide condensation resins having excellent high-temperature properties. This series of reactions is delineated below.

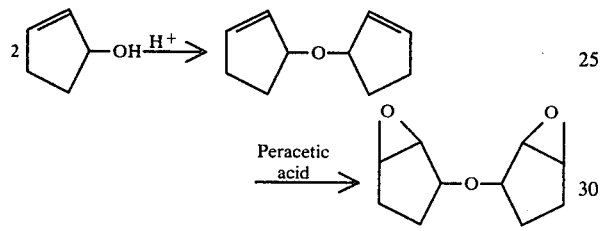

It is therefore an object of this invention to provide a facile means of producing allylic cycloalkenols.

It is a further object to produce allylic cycloalkenols by a rapid oxidation of cycloalkenes to their corresponding allylic cycloalkenols and/or allylic cycloalkenol esters with a minimum of formation of by-products, such as, ketones and high boiling resinous materials.

It is still a further object to effect the production of allylic cycloalkenols at a high efficiency.

It is known that the autoxidation of hydrocarbons proceeds by a free-radical chain reaction to form hydroperoxides as the primary product. When certain soluble metal salts are present, they can react with the hydroperoxides to give free radicals, thereby starting new reaction chains and speeding up the reaction. This is illustrated below for the oxidation of cyclopentene in the presence of cobalt salts.

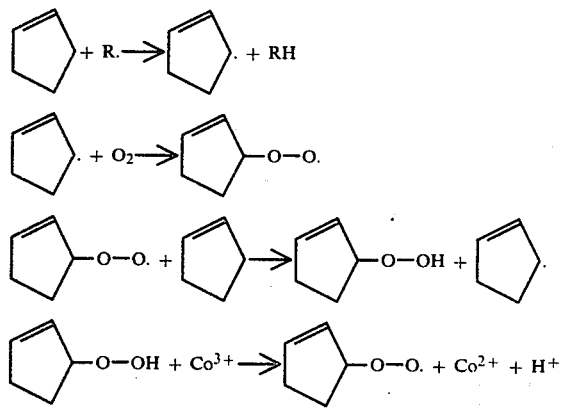

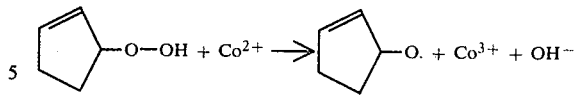

Cobalt salts are particularly strong catalysts for autoxidation and hydrocarbons. Other metal salts, such as those of copper, will react with hydroperoxides in only one way and therefore do not behave as true catalysts since they cease to provide a source of radicals when all of the metal ions have been converted to the "inactive" valence state. In the case of copper it is the cuprous ion which can furnish radicals by the reaction:

$$Cu^+ + ROOH \rightarrow Cu^{++} + OH^- + RO\cdot$$

It is known that cupric ions are good oxidizing agents for converting free radicals to carbocations. In the case of cyclopentenyl radical a reaction would be:

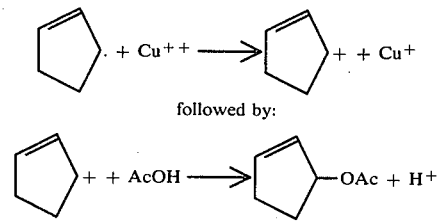

followed by:

The usefulness of cobalt salts for catalyzing the autoxidation of cyclohexene was described in U.S. Pat. No. 2,223,500. It was stated herein that the principal product was 2-cyclopentenone, the principal by-product which is to be avoided in the instant invention.

The activating effect of carboxylic acids on the cobalt-catalyzed autoxidation of hydrocarbons has also been described. (E. H. Farmer et al., J.C.S., 1942, 121-30).

In British Pat. No. 635,054, the use of a combination of cobalt and copper acetates for the oxidation of acetaldehyde to acetic acid and acetic anhydride was described. This combination was also used by Union Carbide Corp. in the oxidation of acetaldehyde to these products.

The use of chain-transfer agents to improve the efficiency of 2-cycloalkenol and its ester has not been described in the prior art though there are many examples of toluene, acetone, and other solvents with chain-transfer properties being used as solvents to the autoxidation of other types of substrates. In such examples, the solvents were used for their solvent properties and not for their chain-transfer properties.

Allylic oxidation of olefins is a common phenomenon and has often been conducted in either the liquid or vapor phase in the presence of various types of catalysts or initiators or even, sometimes in their absence. Cyclopentene is particularly susceptible to oxidation by a free radical mechanism. Criegee et al. has shown in Ber. 72, 1799-1804 (1939) that liquid-phase autoxidation at 20° C. initiated by ultraviolet light gave 2-cyclopentenyl hydroperoxide as the initial product. Van Sickle et al., J.A.C.S. 87, 4824-32 and 4832-37 (1965) obtained similar results using 2,2'-azobisisobutyronitrile (ABN) and 2-cyclopentenyl hydroperoxide itself as initiators.

Synder et al. *J.A.C.S.* 81, 4299-4300 (1959) claimed that the light-catalyzed liquid-phase autoxidation of cyclopentene in the presence of acetic anhydride gave cyclopentenone and 2-acetoxy-3,4-dihydro-[2H]-pyran.

The use of transition metal compounds as catalysts for the liquid-phase oxidation of hydrocarbons has been the subject of several studies.

There is a dearth of information on the metal-catalyzed autoxidation of cyclopentene in the literature. Of that available the following is representative:

Collman et al., *J.A.C.S.* 89, 4809-11 (1967), conducted the autoxidation of cyclopentene using iridium and rhodium complexes as catalysts to produce cyclopentenone and cyclopentene oxide.

East German Pat. No. 81650 issued on May 5, 1971 discloses the use of $Rh(P\phi_3)_3Cl$ and a large amount of t-butyl hydroperoxide (with oxygen) for the oxidation of cyclopentene at 45° C. This reaction was slow giving 2-cyclopentenol in 7% yield along with 10% of 2-cyclopentenone.

Several liquid-phase autoxidations of cyclohexene have been described in the literature. Gould et al., *Journal of Catalysis* 13, 238-44 (1969) showed that the principal volatile products were cyclohexene oxide, 2-cyclohexenone, 2-cyclohexenol, and 2-cyclohexenyl hydroperoxide.

SUMMARY OF THE INVENTION

It has now been found that the objects enumerated above have been achieved for the preparation of allylic cycloalkenols and/or allylic cycloalkenol esters by an autoxidation process which comprises contacting a cyclomonoolefin having 5 to 8 carbons in a liquid phase in the presence of at least about 0.05 mols per mol of cyclomonoolefin of an organic acid activator, having one carboxyl group, 1 to about 10 carbon atoms and free of aliphatic ethylenically unsaturated groups, with an oxygen-containing gas and a catalytic amount of a mixture of cobalt and copper compounds which are soluble in the organic acid at a temperature of about 30° to about 150° C. for a time sufficient to produce allylic cycloalkenols.

Representative cobalt compounds include inorganic salts, such as, cobalt chloride, cobalt bromide, cobalt iodide, cobalt perchlorate, cobalt nitrate, cobalt carbonate, and the like; organic salts, such as, cobalt formate, cobalt acetate, cobalt propionate, cobalt butyrate, cobalt 2-ethylhexoate, cobalt palmitate, cobalt stearate, cobalt chloroacetate, cobalt p-toluenesulfonate, cobalt benzoate, cobalt p-ethylbenzoate, cobalt naphthoate, cobalt acetylacetonate, dicobalt octoacarbonyl, cyclopentadienyl, cobalt dicarbonyl, and the like.

Any compound which can introduce soluble cobalt into the reaction mixture may be used (whether in the cobaltous, cobaltic or zerovalent state), since the original compound does not preserve its identify in the solution.

Representative copper compounds include inorganic salts, such as, copper halides, perchlorates, nitrates, sulfates, and the like; organic salts of aliphatic acids having 1 to 18 carbons, such as, cuprous or cupric formate, acetate, chloracetate, propionate, butyrate, 2-ethylhexoate, palmitate, oleate, and the like; as well as salts of aromatic acids having 6 to about 10 carbons, such as, benzoates, benzenesulfonates and the like. Any compound which introduces copper into the reaction mixture can be used.

The term catalytic amount is used herein to mean dissolved amounts of either cobalt or copper compounds ranging from about 0.01 to about 5% based on the total weight of the reaction mixture.

The term "oxygen-containing gas" is used herein to include pure oxygen as well as mixtures of oxygen with such inert gases as nitrogen, carbon dioxide, neon, argon, krypton and the like, containing at least about 2% by volume of oxygen and preferably less than about 15% by volume of oxygen.

This autoxidation process not only can be practiced in one step as described supra, but also as a two-step process wherein the cycloolefin is first autoxidized by oxygen to a hydroperoxide which is then decomposed in the presence of soluble cobalt and copper compounds.

The organic acid is not narrowly critical and can be a saturated aliphatic monocarboxylic acid, such as, formic, acetic, propionic, halosubstituted acetic acids and the like; aromatic monocarboxylic acids, such as, benzoic, toluic, halosubstituted benzoic acids and the like; arylalkyl monocarboxylic acids, such as, phenylacetic, phenylpropionic, halogen substituted phenylacetic acids, and the like.

Although as little as about 0.05 mols of organic acid can be used, it is preferred to use about 0.5 to about 5.0 mols per mol of cycloolefin.

Although temperatures of about 30° to about 150° C. can be used a preferred range is about 45° to about 130° C.

If desired, chain transfer agents can optionally be used in preferred amounts of about 0.2 to about 1.0 mol per mol of cycloolefin. Representative examples of chain transfer agents include substituted aromatic hydrocarbons having 7 to 12 carbons and hydrogen atoms alpha to an aromatic ring carbon atom, such as, cumene, tetralin, p-diisopropylbenzene, ethylbenzene and the like; cycloparaffins having 5 to 7 carbons, such as cyclopentene, cyclohexane or methylcyclohexane; $C_4-C_6$ isoparaffins, such as, isobutane, isopentane, or isohexane; and aliphatic ethers, alcohols or ketones having alpha hydrogens, such as methyl ethyl ketone, acetone, isopropanol, methanol, diisopropyl ether and the like.

Pressure is not critical and so superatmospheric as well as subatmospheric pressures can be used. A suggested range is about 0.8 to about 60 atmospheres with 1.0 to 30 atmospheres being a preferred range.

The invention is further described in the examples which follow. All parts and percentages are by weight unless otherwise specified.

EXAMPLES 1-3

A vertical cylindrical glass reactor, equipped with a gas-diffusing inlet at the bottom, a reflux condenser cooled with solid carbon dioxide (in acetone), a thermocouple well, and a glass jacket for heating purposes was charged with a solution containing cyclopentene, acetic acid, and catalyst. The mixture was heated to 45° C. by acetone vapors (from an external boiler) under reflux in the jacket. Oxygen was introduced through the diffuser at such a rate as to produce only a small blowoff. There was no provision for stirring the reaction mixture since good mixture was effected by the rising bubbles of oxygen. After a short induction period of 10 to 15 minutes the reaction proceeded rapidly, and the temperatures rose to its maximum value. Reaction was terminated when the conversion of cyclopentene was estimated to have reached 20 to 30 percent, and the solution was then analyzed by gas chromatography. Samples were also evaporated to dryness in a 150° C. oven under a flow of nitrogen gas to determine the amount of non-volatile (resinous) by-product.

The results of three examples conducted in the above fashion are shown in Table I. These results show the effect of acetic acid on the reaction and also the benefit of using a copper salt along with the cobalt salt catalysts. When an attempt was made to oxidize under these conditions with a copper salt alone, no reaction took place.

TABLE I

Autoxidation of Cyclopentene at Atmospheric Pressure Catalyst and Acetic Acid Effects

| Example No.→ | 1 | 2 | 3 |
|---|---|---|---|
| C$_5$H$_8$ (mols) | 1.0 | 1.0 | 1.0 |
| AcOH (mols) | 0 | 1.0 | 1.0 |
| Catalysts | CoNaph. (0.4)* | Co(OAc)$_2$ (0.4) | Co(OAc)$_2$ (0.4) |
| (millimols) | CuNaph. (0.9)* | — | Cu(OAc)$_2$ (2.5) |
| Temper °C. (max) | 46° | 55° | 46° |
| Time (min.) | 120 | 90 | 50 |
| Conversion (%) | 22 | 32 | 25 |
| Yields: | | | |
| —OH (%) | 2.6 | 7.9 | 7.0 |
| —OAc (%) | 0 | 0 | 2.1 |
| =O (%) | 5.1 | 6.0 | 4.9 |
| O (%) | 0.5 | 2.2 | 1.9 |
| Residue (g)⊕ | — | 3.7 | 0.21 |
| Efficiency (%) | 12 | 25 | 36 |

$$\text{Yield (\%)} = \frac{\text{mols of product}}{\text{mols cyclopentene charged}} \times 100$$

Efficiency (%) =

$$\frac{(\text{mols} \bigcirc\text{—OH}) + (\text{mols} \bigcirc\text{—OAc})}{(\text{mols} \bigcirc \text{charged}) - (\text{mols} \bigcirc \text{recov.})} \times 100$$

*Naphthenate catalysts were added as 6% solutions in naphtha.
⊕Residue weights are corrected for catalyst content.

EXAMPLES 4–7

A series of autoxidation reactions were conducted with varying amounts of acetic acid using the glass apparatus previously described in Examples 1–3. The results are delineated in Table II. In addition to demonstrating that very little acetic acid is required, these examples showed the benficial effect of giving the reaction mixture at thermal "post treatment" after terminating the introduction of oxygen. This thermal "post treatment" consists in heating the reaction mixture at a temperature of about 75° C. to about 140° C. for about 2 hours to about 3 minutes with the proviso that the time of treatment is shortened as the temperature is increased. It will be noted that the "post treatment" was beneficial in all cases, but that when a large amount of acetic acid was used a considerable esterification of the cyclopentenol took place in the post treatment step with the result that the principal product was the corresponding acetate.

TABLE II

Autoxidation of Cyclopentene (1 Atm.) - Effect of Acetic Acid Concentration and Post Treatment

| Example No. | 4 | | 5 | | 6 | | 7 | |
|---|---|---|---|---|---|---|---|---|
| C$_5$H$_8$ (mols) | 1.0 | (1/1) | 1.25 | (2/1) | 1.25 | (4/1) | 1.25 | (7.4/1) |
| AcOH (mols) | 1.0 | | 0.63 | | 0.32 | | 0.17 | |
| Benzene (mols)* | 0.07 | | 0.07 | | 0.07 | | 0.07 | |
| Catalysts | Co(OAc)$_2$(0.4) | | Co(OAc)$_2$(0.4) | | Co(OAc)$_2$(0.4) | | Co(OAc)$_2$(0.4) | |
| (millimols) | Cu(OAc)$_2$(1.0) | | Cu(OAc)$_2$(1.0) | | Cu(OAc)$_2$(1.0) | | Cu(OAc)$_2$(1.0) | |
| | | PT+ | | PT+ | | PT+ | | PT+ |
| Temp. (°C.) | 53 | 120 | 50 | 100 | 50 | 100 | 47 | 100 |
| Time (min.) | 120 | 10 | 120 | 60 | 120 | 60 | 120 | 60 |
| Conversion (%) | 24 | 29 | 21 | 24 | 18 | 21 | 21 | 24 |
| Yields: | | | | | | | | |
| 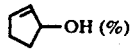—OH (%) | 7.1 | 3.3 | 5.8 | 4.4 | 6.4 | 5.5 | 5.5 | 7.8 |
| 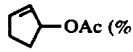—OAc (%) | 2.5 | 9.0 | 2.4 | 6.6 | 2.1 | 5.0 | 1.4 | 3.5 |
| =O (%) | 3.6 | 3.3 | 2.9 | 2.6 | 3.2 | 2.5 | 3.1 | 2.7 |
| 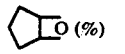O (%) | 1.6 | 0.6 | 1.3 | 0.6 | 1.3 | 0.4 | 1.1 | 1.2 |
| ROOH (mols) | 0.022 | 0 | 0.021 | 0 | 0.025 | 0 | 0.04 | 0 |
| ROOR' (mols) | 0.078 | 0 | 0.11 | 0 | 0.090 | 0 | — | 0 |
| Residue (g) | — | — | 0.6 | — | 0.5 | — | 0.6 | — |
| Efficiency(%) | 40 | 44 | 39 | 46 | 48 | 50 | 33 | 48 |

TABLE II-continued

Autoxidation of Cyclopentene (1 Atm.) - Effect of
Acetic Acid Concentration and Post Treatment

| | | | | | | | | |
|---|---|---|---|---|---|---|---|---|
| Ratio 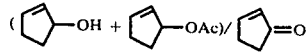 | 2.7 | 3.7 | 2.8 | 4.3 | 2.7 | 4.3 | 2.2 | 4.1 |

*Benzene, weighed accurately to 10⁻⁴g, was added as an internal standard.
¹ Data under PT show the effect on giving the reactor product a post treatment to utilize the hydroperoxide content and destroy other peroxides.
′ Y = H or Ac—. The ratio,

is of particular interest since cyclopentenone is the major by-product. The fact that the cyclopentenone appears to decrease on post treatment suggests that hydroperoxides in the pretreatment sample are converted in part to cyclopentenone in the gas chromatograph.

EXAMPLE 8

The autoxidation of cyclopentene was conducted in the same fashion as described in Examples 1–3 but with the use of pivalic in place of acetic acid. The conditions and results are summarized below:

Charged:
Cyclopentene: 1.0 mol
Pivalic acid: 0.5 mol
Co(OAc)$_2$.4H$_2$O: 0.004 mol
Cu(OAc)$_2$.H$_2$O: 0.0015 mol
Temperature (max): 57° C.
Time: 140 minutes
Post treatment: 10 minutes at 120° C.
Yields (based on cyclopentene charged):

| | Before Post Treatment | After Post Treatment |
|---|---|---|
| 2-Cyclopentenol | 9.9% | 11.7% |
| 2-Cyclopentenyl pivalate | 3.2 | 3.3 |
| 2-Cyclopentenone | 6.3 | 6.8 |
| Cyclopentene oxide | 2.1 | 2.2 |
| Conversion: | 32 | 35 |
| Efficiency to 2-cyclopentenol and | | |
| 2-cyclopentenyl pivalate | 41% | 43% |

It can be seen that the amount of ester formed with pivalic acid was low and that no additional pivalate was formed during the post treatment.

EXAMPLES 9–24

The effect of various chain transfer agents on the autoxidation of cyclopentene was investigated using the apparatus and general procedures described in Examples 1–3. Table III summarizes the reaction conditions and the results of analyses conducted without post treatment of the reaction mixtures.

It was of interest to determine the extent of oxidation of the chain transfer agent used in these examples. In the case of Example 20, 14% of the cumene was oxidized to alpha-cumenol (dimethylphenylcarbinol).

TABLE III

Effect of Chain Transfer Agents on Autoxidation of
Cyclopentene in Acetic Acid Using Co$^{++}$ and Cu$^{++}$ Catalysts

| Example No. | CT Agent | Mol Ratio Charged C$_5$H$_8$AcOH/CT | C$_5$H$_8$ Converted (and/or Lost) | Mol Ratio of CpOH + CpOAc to Cp=0 | Efficiency to CpoH + CpOAc |
|---|---|---|---|---|---|
| 9 | None | 1/1/0 | 24% | 2.7 | 44% |
| 10 | Cumene | 1/1/0.5 | 32 | 3.5 | 60 |
| 11 | Cumene | 1/1/0.5 | 49 | 3.0 | 46 |
| 12 | Tetralin | 1/1/0.5 | 27 | 3.0 | 47 |
| 13 | Tetralin | 1/1/0.5 | 39 | 2.6 | 38 |
| 14 | Tetralin | 1/1/0.25 | 28 | 3.5 | 47 |
| 15 | p-Diisopropylbenzene | 1/1/0.5 | 27 | 3.0 | 54 |
| 16 | Ethylbenzene | 1/1/0.5 | 35 | 3.0 | 50 |
| 17 | Methyl ethyl ketone | 1/0.5/0.25 | 31 | 3.3 | 48 |
| 18 | Isopropanol | 1/1/0.5 | 28 | 3.0 | 42 |
| 19 | Diisopropyl ether | 1/0.5/0.25 | 35 | 2.8 | 39 |
| Lower Conversion Runs: | | | | | |
| 20 | Cumene | 1/1/0.25 | 20 | 3.4 | 56 |
| 21 | Acetone | 1/1/0.5 | 20 | 3.0 | 53 |
| 22 | Methanol | 1/1/0.5 | 19 | 3.9 | 41 |
| 23 | Cyclohexane | 1/1/0.5 | 21 | 2.5 | 58 |
| 24 | 2,2,4-Trimethylpentane | 1/1/0.5 | 23 | 1.7 | 41 |

C$_5$H$_8$ = Cyclopentene
CpOH = 2-Cyclopentenol
CpOAc = 2-Cyclopentenyl acetate
Cp = 0 = 2-Cyclopentenone
CT = Chain transfer agent
"Efficiency" is percent of theoretical yield derivable from the cyclopentene consumed and/or lost.

REACTION PROCEDURE FOR PRESSURE OXIDATIONS OF EXAMPLES 25–29

A standard one-liter autoclave was charged with a reaction mixture. The autoclave was then heated to the desired temperature and was then pressurized to 400 psi with nitrogen. Oxygen was then charged into the autoclave bringing the total pressure to 430 psi. Further oxygen was added, as it was depleted, in 10 psi increments so that the total pressure never exceeded 430 psi. After the desired amount of oxygen was added, the reactor was immediately emptied and the product was collected in a container cooled with solid carbon dioxide.

EXAMPLE 25

The autoclave was charged with a solution containing 0.05 g of $Cu(OAc)_2.H_2O$, 0.10 g of $Co(OAc)_2.4H_2O$, 54.0 g glacial acetic, 184.0 g of cyclopentene (Velsicol Corporation, 95%), and 15.3802 g of chlorobenzene, which was used as an internal standard. The autoclave was then heated to 100° C. and was pressurized to 400 psi with nitrogen. The pressure was then brought to 430 psi with oxygen which was replenished in 10 psi increments as used. After a total of 250 psi of oxygen had been added, the reactor was discharged. The temperature over the course of the reaction varied from 103° to 114° C.

The product was analyzed by gas chromatography based on the chlorobenzene internal standard. Residue was determined by taking 30 g samples of the product and heating to 100° C. for 0.5 hours at full pump vacuum. Results are indicated in Table IV.

EXAMPLE 26

Example 25 was repeated with the exception that the following charge was used;
- $Cu(OAc)_2.H_2O$: 0.1 g
- $Co(OAc)_2.4H_2O$: 0.50 g
- Chlorobenzene: 9.965 g
- Glacial acetic acid: 54.0 g
- Cyclopentene: 184.0 g Results are presented in Table IV.

EXAMPLE 27

Example 25 was repeated with the exception that the following charge was used:
- $Cu(OAc)_2.H_2O$: 0.36 g
- Chlorobenzene: 17.7234 g
- Glacial acetic acid: 54.0 g
- Cyclopentene: 184.0 g Results are shown in Table IV.

EXAMPLE 28

Example 25 was repeated with the exception that the following charge was used:
- $Co(OAc)_2.4H_2O$: 0.32 g
- Chlorobenzene: 17.8511 g
- Glacial acetic acid: 54.0 g
- Cyclopentene: 184.0 g Results are presented in Table IV

EXAMPLE 29

Example 25 was repeated with the exception that the following charge was used:
- $Cu(OAc)_2.H_2O$: 0.3008 g
- $Co(OAc)_2.4H_2O$: 0.0507 g
- Chlorobenzene: 17.7935 g
- Glacial acetic acid: 54.0 g
- Cyclopentene: 184.4 g Results are shown in Table IV.

EXAMPLE 30

Example 25 was repeated with the exception that the following charge consisted of:
- $Cu(OAc)_2.H_2O$: 0.50 g
- $Co(OAc)_2.4H_2O$: 0.10 g
- Glacial acetic acid: 57.0 g
- Cyclopentene: 194.4 g A total of 300 psi of oxygen was added in the course of the reaction. Analyses were performed by gas chromatography after addition of chlorobenzene as an internal standard to the reaction product. The results are presented in Table IV.

COMMENTS ON EXAMPLES 25–30

Examples 25 and 26 show a wide range of catalyst ratios giving good results.

Examples 27 and 28 show inferior results when catalysts are not used in combination.

Example 29 shows that the better results shown in Examples 25 and 26 are not due to the slightly larger amounts of catalysts present.

Example 30 shows that the presence of chlorobenzene in the reaction mixture did not have a significant effect on efficiencies. The efficiency to the desired products was higher in this experiment than in the experiments conducted with copper alone (Example 27) or cobalt alone (Example 28) even though more oxygen had been added and the reaction had been taken to higher conversion.

TABLE IV

| Example No. | 25 | 26 | 27 | 28 | 29 | 30 |
|---|---|---|---|---|---|---|
| Catalyst concentration (weight % of charge) | | | | | | |
| $Cu(OAc)_2 . H_2O$ | .20 | .04 | .14 | — | .12 | .20 |
| $Co(OAc)_2 . 4H_2O$ | .04 | .20 | — | .12 | .02 | .04 |
| Oxygen added (psi/mol cyclopentene) | 92 | 92 | 92 | 92 | 92 | 105 |
| Conversion (%) | 16 | 15 | 14 | 18 | 15 | 22 |
| Efficiency to (%) | | | | | | |
| epoxycyclopentane | 14 | 15 | 11 | 11 | 15 | 13 |
| 2-cyclopentenol | 33 | 36 | 24 | 39 | 34 | 31 |
| 2-cyclopentenone | 10 | 8 | 13 | 13 | 11 | 13 |
| 2-cyclopentenyl acetate | 33 | 30 | 28 | 13 | 28 | 28 |
| other volatiles | 5 | 4 | 10 | 9 | 3 | 8 |
| residue | 5 | 7 | 14 | 14 | 8 | 7 |
| cyclopentenol + acetate | 66 | 66 | 52 | 53 | 62 | 59 |

EXAMPLE 31

A one-liter autoclave was charged with 204.4 g of cyclopentene and heated to 100° C. The autoclave was pressurized to 300 psi with nitrogen and then to 330 psi with oxygen (i.e., "30 psi of oxygen" was added). The oxygen was replenished in 10 psi increments as it was depleted, keeping the total pressure below 330 psi. After a total of 330 psi of oxygen was added, the autoclave was cooled. The product was left in the autoclave 20 hours before emptying.

Iodimetric titration of the product solution showed it contained 6.9 weight percent cyclopentenyl hydroperoxide.

EXAMPLE 32

To a 5.00 aliquot of the cyclopentenyl hydroperoxide solution made in Example 31, was added 0.2524 g of chlorobenzene (internal standard for gas chromatographic analysis) and 1.00 ml of a solution made by dissolving 0.10 g of cupric acetate monohydrate in 10.0 g of glacial acetic acid. This solution was tightly capped and placed in a 100° C. oil bath for 1½ hrs. The product was then analyzed by gas chromatography. The results are shown in Table V. Iodimetric titration of the product solution showed no hydroperoxide.

EXAMPLE 33

Reaction was performed as in Example 32 except with the following charge:
500 ml of cyclopentenyl hydroperoxide solution made in Example 31;
0.2446 g chlorobenzene internal standard;
1.00 ml of a solution of 0.10 g of cobaltous acetate tetrahydrate in 10.0 g glacial acetic acid.
The results of this Example are given in Table V. Iodimetric titration showed no remaining hydroperoxide.

EXAMPLE 34

Reaction was carried out as in Example 32 except with the following charge:
5.00 ml of cyclopentenyl hydroperoxide solution made in Example 31;
0.3080 g of chlorobenzene internal standard;
1.00 ml of a solution of 0.0836 g of cupric acetate monohydrate and 0.0167 g of cobaltous acetate tetrahydrate in 10.0 g of glacial acetic acid.
Results are presented in Table V. Iodimetric titration showed no remaining hydroperoxide.

EXAMPLE 35

A 5.00 ml aliquot of cyclopentenyl hydroperoxide solution from Example 31 was mixed with 0.2495 g of chlorobenzene and was placed in a tightly capped tube. The tube was heated in a 120° C. oil bath for 5 hours and then was analyzed by gas chromatography. Iodimetric titration showed that 8% of the original hydroperoxide remained in the product solution. Results are presented in Table V.

Example 31 shows the uncatalyzed autoxidation. Even after 20 hours in the autoclave large amounts of hydroperoxide remained.

Examples 32 and 33 show the decomposition of cyclopentenyl hydroperoxide containing solutions with single metal catalysts.

Example 34 shows that the combined metal catalyst results in better efficiencies to cyclopentenol plus cyclopentenyl acetate. Hydroperoxide was decomposed to give more mols of product than with individual catalysts.

Example 35 shows uncatalyzed decomposition of cyclopentenyl hydroperoxide containing solution. Although a higher temperature and much longer reaction time was used, some peroxide was left decomposed. The combined efficiency to the desired products was much lower.

TABLE V

| Example No. | 32 | 33 | 34 | 35 |
|---|---|---|---|---|
| Catalyst | $Cu^{++}$ | $Co^{++}$ | $Cu^{++}/Co^{++}$ | None |
| Mol percent of products detected by gas chromatography: | | | | |
| epoxycyclopentane | 17 | 15 | 14 | 21 |
| cyclopentenol | 39 | 47 | 42 | 45 |
| cyclopentenone | 19 | 17 | 16 | 20 |
| cyclopentenyl acetate | 17 | 5 | 19 | — |
| others | 8 | 16 | 10 | 15 |
| total cyclopentenol acetate | 56 | 52 | 61 | 45 |
| Total millimols of detected products | 10.3 | 10.6 | 13.4 | 10.0 |

Although the invention was described in its preferred forms, it will be understood by those skilled in the art that many changes may be made without departing from the spirit and scope of the invention.

What is claimed is:

1. Method of preparing allylic cycloalkenols and/or allylic cycloalkenol esters by an autoxidation process which comprises contacting a cyclomonoolefin having 5 to 8 carbons selected from the group consisting of cyclopentene, methylcyclopentenes, cyclohexene, cycloheptene and cyclooctene in a liquid phase in the presence of at least about 0.05 mol, per mol of cyclomonoolefin of an organic acid activator having one carboxyl group, 1 to about 10 carbons and free of aliphatic ethylenically unsaturated groups selected from the class consisting of saturated aliphatic monocarboxylic acids, aromatic monocarboxylic acids, halosubstituted benzoic acids, and arylalkyl monocarboxylic acids, with an oxygen-containing gas and a catalytic amount of a mixture of cobalt and copper compounds which are soluble in the organic acid at a temperature of about 30° to about 150° C. for a time sufficient to produce allylic cycloalkenols and/or allylic cycloalkenol esters of one of said organic acids.

2. Method claimed in claim 1 wherein the organic acid is acetic acid.

3. Method claimed in claim 1 wherein the cyclomonoolefin is cyclopentene.

4. Method claimed in claim 1 wherein the cyclomonoolefin is cyclohexene.

5. Method claimed in claim 1 wherein the concentration of oxygen in the oxygen-containing gas is at least 2% by volume.

6. Method claimed in claim 1 wherein a chain transfer agent is present at a concentration of about 0.2 to about 1.0 mol per mol of cyclomonoolefin.

7. Method claimed in claim 1 wherein the amount of carboxylic acid is about 0.5 to about 5.0 mols per mol of cyclomonoolefin.

8. Method claimed in claim 1 wherein the temperature is in the range of about 45° C. to about 130° C.

9. Method claimed in claim 1 wherein the pressure is in the range of about 0.8 to about 60 atmospheres.

10. Method claimed in claim 1 wherein the cobalt and copper compounds are cobaltous acetate and cupric acetate respectively.

11. Method claimed in claim 1 wherein the final reaction mixture after terminating the introduction of the oxygen-containing gas is subjected to a post treatment consisting of heating said final reaction mixture at a temperature of about 75° C. to about 140° C. for about 2 hours to about 3 minutes.

12. Method of preparing allylic cycloalkenols and/or allylic cycloalkenol esters which comprises contacting a cyclomonoolefin having 5 to 8 carbons in a liquid phase with an oxygen-containing gas until an allylic cycloalkenyl hydroperoxide is formed and then contacting said allylic cycloalkenyl hydroperoxide with a catalytic amount of a mixture of cobalt and copper compounds in the presence of at least about 0.05 mol, per mol of cyclomonoolefin charged of an organic acid activator, in which said cobalt and copper compounds are soluble, having one carboxyl group, 1 to about 10 carbons and free of aliphatic ethylenically unsaturated groups selected from the class consisting of saturated aliphatic monocarboxylic acids, aromatic monocarboxylic acids, halosubstituted benzoic acids, and arylalkyl monocarboxylic acids at a temperature of about 30° to about 150° C. for a time sufficient to produce allylic cycloalkenols and/or allylic cycloalkenol esters of one of said organic acids.

* * * * *